United States Patent [19]

Scopes

[11] Patent Number: 4,623,625
[45] Date of Patent: Nov. 18, 1986

[54] ENZYME EXTRACTION AND PURIFICATION PROCESSES

[75] Inventor: Robert K. Scopes, Melbourne, Australia

[73] Assignee: La Trobe University, Victoria, Australia

[21] Appl. No.: 686,264

[22] PCT Filed: Apr. 19, 1984

[86] PCT No.: PCT/AU84/00069
§ 371 Date: Dec. 12, 1984
§ 102(e) Date: Dec. 12, 1984

[87] PCT Pub. No.: WO84/04329
PCT Pub. Date: Nov. 8, 1984

[30] Foreign Application Priority Data

Apr. 21, 1983 [AU] Australia ............................... PF8995
Jan. 3, 1984 [AU] Australia ............................... PG3049

[51] Int. Cl.$^4$ ........................... C12N 9/04; C12N 9/12
[52] U.S. Cl. ..................................... 435/190; 435/194; 435/814
[58] Field of Search ................................ 435/190, 194

[56] References Cited

PUBLICATIONS

Wills et al, Archives of Biochemistry and Biophysics, vol. 210, No. 2, pp. 775-785, Sept. 1981.
Methods in Enzymology, vol. 89, pp. 258-275, (1982).
Williamson et al, "Properties of Drosophila NADP+-Isocitrate Dehydrogenase Purified on Procion Brilliant Blue-Sepharose-4B", Conf. Biochem. Physiol. B. (1980), 65B(2), pp. 339-343.
Watson et al, "The Selective Retardation of NADP+-Dependent Dehydrogenases by Immobilized Procion Red HE-3B", Biochem. Journal (1978), 173(2), pp. 591-596.
Beissner et al, "Immobilized Anthraquinone Dyes for Affinity Chromatography", J. Chromatogr. (1978), 161, pp. 127-135.
Hey et al, "Tandem Dye-Ligand Chromatography and Biospecific Elution Applied to the Purification of Glucose-6-Phosphate Dehydrogenase from *Leuconostoc mesenteroides*", Biochem. Journal, (1983), 209, pp. 363-371.
Hey et al, "The Value of Screening in Dye-Ligand Chromatography", Proceedings of Symposium on Affinity Chromatography, Eindhoven, Jun. 1981 (Abstract).

*Primary Examiner*—Lionel M. Shapiro
*Attorney, Agent, or Firm*—Armstrong, Nikaido, Marmelstein & Kubovcik

[57] ABSTRACT

A process for the preparation of an enzyme extract containing glucose 6-phosphate dehydrogenase, glucokinase, pyruvate kinase and fructokinase, derived from microorganism cells, by subjecting *Zymomonas mobilis* bacterium cells to extraction with an extraction medium comprising a partially water-miscible organic solvent; a non-ionic surfactant; and lysozyme; under neutral to alkaline pH conditions to provide an extract containing said enzymes. The process can be integrated with a process for the sequential isolation of the glucose 6-phosphate dehydrogenase, glucokinase, pyruvate kinase and fructokinase, present in the enzyme extract, by sequentially contacting the extract in a buffer with a plurality of affinity chromatography adsorbents each of which is a protein-binding dye bound to a support matrix and selective with respect to said enzymes so that glucose 6-phosphate dehydrogenase and glucokinase are isolated from the extract by the correspondingly selective adsorbent, followed by isolation of pyruvate kinase and fructokinase by the correspondingly selective adsorbents, then elution to recover each enzyme from the correspondingly selective adsorbent of said plurality of adsorbents, with optional purification of each enzyme.

35 Claims, 4 Drawing Figures

ENZYME EXTRACTION AND PURIFICATION PROCESSES

BACKGROUND OF THE INVENTION

The present invention relates to processes for the extraction and purification on an industrial scale of commercially useful enzymes which can be derived from the bacterium *Zymomonas mobilis* (hereinafter for convenience referred to simply as *Z. mobilis*), in containing high levels of enzymes of the Entner-Doudoroff pathway and being an excellent source for isolating these enzymes, besides having associated enzymes at high levels which are involved in the fermentation of sugars to alcohol.

Enzymes which can be extracted from *Z. mobilis* and purified on an industrial scale by the processes of the invention are as follows:

Glucose 6-phosphate dehydrogenase EC 1.1.1.49
Glucokinase EC 2.7.1.2
Pyruvate kinase EC 2.7.1.40
Fructokinase EC 2.7.1.4 each of which has an established commercial usefulness.

Glucose 6-phosphate dehydrogenase, which is currently available from biochemical reagent suppliers, is useful as a component in clinical diagnostic reagents for determining glucose, ATP, other sugars, and for enzyme activity measurements. These uses extend to the industrial field, specifically the food industry, with respect to analytical methods for estimating sugars, and to the biochemical field, with respect to forensic science, genetics and microbiology research for enzyme activity measurements, measurements of sugars, ATP, and the like.

Glucokinase, which is likewise available, is useful specifically for clinical and food analysis for measuring glucose, ATP, and certain enzymes such as creatine kinase in clinical diagnostic tests. Pyruvate kinase, which is likewise available, is useful specifically for enzyme activity measurements when the enzyme concerned is a kinase, its use mainly being in clinical and biological research, however, it is also valuable in an ATP-regeneration system for chemical and biochemical synthesis where ATP is consumed in the reaction. Fructokinase, which is likewise available, is useful specifically for measuring fructose in the presence of glucose, which is a test valuable in the food industry.

Glucose 6-phosphate dehydrogenase is present in microbial cells other than *Z. mobilis*, for instance, *Leuconostoc mesenteroides* (hereinafter referred to simply as *L. mesenteriodes* for convenience) or other microorganisms containing NAD-specific glucose 6-phosphate dehydrogenase. Extraction and purification of the enzyme on an industrial scale from such cells presents problems and involves many technical difficulties.

Industrial production of intracellular enzymes can be considered to involve three distinct phases, namely: (i) propagation of the microbial cells and their recovery in paste form from the propagation medium; (ii) extraction of the microbial cells paste to provide the raw material for isolation of the enzymes; and (iii) isolation and purification of the enzymes from the extract of that raw material.

Methods for the propagation of microbial cells such as *L. mesenteroides* and *Z. mobilis* are known. Also, several different methods have been described for the extraction of microbial cells. For instance, physicochemical methods involve osmotic shock [Schwinghamer, E. A. (1980) *FEMS Microbiology Letters.* 7, 157–162], lysozyme treatment [Saint-Blacard, J., Mawal, J. P. Constant, J. F., Berthon, J. and Jolles, P. (1981) *Bioscience Reports.* 1, 119–123], organic solvents [Rutter, W. J. and Hunsley, J. R. (1966) *Methods Enzymol.* 9, 480–486 ], and detergents [Miozari, G. F., Niederberger, P. and Hutter, R. (1978) *Analyt. Biochem.* 90, 220–233]. Mechanical methods can also be used successfully.

The ability of microbial cells such as *L. mesenteroides* and *Z. mobilis* cells to lyse and release enzymes into solution is largely dependent upon the conditions under which those cells are grown. For example, when those cells are harvested in conditions of (i) high temperature, (ii) high alcohol level, and (iii) low pH, they are more likely to lyse easily than if the conditions are more moderate.

In that alcohol is the product of *Z. mobilis* fermentation, high yields of cells can only be obtained in the presence of alcohol, however, the temperature and pH of the cultivation media may be varied according to the degree of strength required in the cells to resist lysis prior to harvesting.

Thus, a problem with purposely growing so-called "weaker" cells is that they are liable to lyse prior to harvesting and during transportation for extraction, thereby reducing yield of the desired enzyme. On the other hand, so-called "tough" cells are much more difficult to lyse during harvesting. A reliable method for extracting both "weak" and "tough" cells equally well is needed.

In that somewhat equivalent problems to those indicated above in relation to the production and extraction of *Z. mobilis* cells for recovery of the enzyme glucose 6-phosphate dehydrogenase, apply for the recovery of the other enzymes listed above, a reliable process for extracting those enzymes from said cells, also is needed.

SUMMARY OF THE INVENTION

The present invention provides: (i) a process for the extraction of said enzymes from *Z. mobilis* cells, which process requires no special apparatus and lysis is completed within 1–2 hours and the total amount of the enzymes can be considered to be maximised in the harvested cells extract, and (ii) processes for the isolation and purification of said enzymes from *Z. mobilis* cells.

Thus, we have developed a process for the preparation of an enzyme extract containing said enzymes and derived from *Z. mobilis* bacterium cells, which process comprises subjecting said cells to extraction with an extraction medium comprising a partially water-miscible organic solvent; a non-ionic surfactant; and lysozyme; under neutral to alkaline pH conditions to provide an extract containing said enzymes. Each of these four factors separately will result in some degree of extraction of the *Z. mobilis* cells, especially "weak" cells, however, we have found that when these factors are combined, they co-act to maximise the total amount of protein and of the enzymes in the extract of "tough" cells also.

And we have also developed a process for the isolation of said enzymes from an extract of *Z. mobilis* which comprises sequentially contacting the extract with a plurality of affinity chromatography adsorbents each of which is a protein-binding dye bound to a support matrix and selective with respect to said enzymes so that a glucose 6-phosphate dehydrogenase and glucokinase are isolated from the extract by the correspondingly selective adsorbent, followed by isolation of pyruvate kinase and fructokinase by the correspondingly selective adsorbents, with elution to recover each enzyme from the correspondingly selected adsorbent of said plurality of adsorbents.

And we have found that these processes can be integrated into a process for the extraction of the enzymes glucose 6-phosphate dehydrogenase, glucokinase, pyruvate kinase and fructokinase from microorganism cells, followed by the sequential isolation of those enzymes from the resultant extract, which comprises: (A) subjecting Z. mobilis bacterium cells to extraction with an extraction medium comprising a partially water-miscible organic solvent; a non-ionic surfactant; and lysozyme; under neutral to alkaline pH conditions to provide an extract containing said enzymes; (B) sequentially contacting the extract with a plurality of affinity chromatography adsorbents each of which is a protein-binding dye bound to a support matrix and individually selective with respect to said enzymes so that glucose 6phosphate dehydrogenase and glucokinase are isolated from the extract by the correspondingly selective adsorbent, followed by isolation of pyruvate kinase and fructokinase by the correspondingly selective adsorbents; with (C) elution to recover each enzyme from the correspondingly selected adsorbent of said plurality of adsorbents.

PREFERRED EMBODIMENTS OF THE INVENTION

In the extraction process of the present invention for the recovery of said enzymes from Z. mobilis cells, the extraction medium comprises partially water-miscible organic solvent preferably in an amount of about 1-2% v/v, more preferably about 1% v/v; non-ionic surfactant preferably in an amount of about 0.05 to 0.2% v/v, more preferably about 0.1% v/v; lysozyme preferably in an amount of about 0.2 to 2 mg/g wet wt. of the cells; and with the pH preferably at between 7.0 and 9.0, more preferably between pH 7.5 and 8.5.

The partially water-miscible organic solvent may be an aromatic hydrocarbon such as toluene, or a lower alkyl ester such as ethyl acetate, or preferably a lower alkanol such as butan-1-ol; the non-ionic surfactant preferably is of the phenyl polyethylene glycol type, such as the products sold under the trade names "Triton" and "Nonidet"; and the alkaline pH conditions preferably are about pH 7.5 or slightly above pH 7.5, for example pH 7.5–8.5.

The advantages obtained in the extraction of Z. mobilis cells according too the process of the invention have been found to be peculiar to those cells when compared with L. mesenteroides cells, in that said process is virtually non-effective for the extraction of L. mesenteroides cells. Also, Z. mobilis cells can be grown in simpler nutrient mixtures than can L. mesenteroides cells; the amount of L. mesenteroides cells obtained per liter of culture is relatively low; there is further difficulty in effecting lysis of L. mesenteroides cells; and there is somewhat more of any of the enzymes listed above, extractable from Z. mobilis cells per g. of cells than from L. mesenteroides cells.

In the isolation and purification processes of the present invention by affinity chromatography, the adsorbent in each case may consist of a so-called triazinyl protein-binding dye, bound to a polymer or copolymer of agarose as support matrix.

Affinity chromatography is known to involve separation of proteins by selective adsorption onto and/or elution from a solid medium, generally in the form of a column. The solid medium is usually an inert carrier matrix to which is attached a ligand having the capacity to bind under certain conditions, the required protein or proteins in preference to others present in the same sample, although in some cases the matrix itself may have such selective binding capacity. The ligand may be biologically complementary to the protein to be separated, for example, antigen and antibody, or may be any biologically unrelated molecule which by virtue of the nature and steric relationship of its active groups has the power to bind the protein.

The support matrices commonly used in association with such protein-binding ligands include, for example, polymers and copolymers of agarose, dextrans and amides, especially acrylamide, or glass beads or nylon matrices. Cellulose and substituted celluloses are generally found unsuitable when using dyes, since, although they bind large amounts of dye, the dye is poorly accessible to the protein, resulting in poor protein binding.

U.S. Pat. No. 4,016,149 and Baird et al, *FEBS Letter*, Vol. 70 (1976) page 61, describe solid media wherein the ligands are mono-chloro-triazinyl dyes and are bound to dextran or agarose matrices by substitution at the chloride group. While binding in alkaline buffered media results in low protein binding capacity, it is possible to increase the dye binding by cyanogen bromide activation of the agarose matrix. However, cyanogen bromide activation has serious disadvantages, especially for industrial and biological use.

U.K. Pat. No. 2015552 describes a method of achieving useful controlled levels of dye binding without the use of cyanogen bromide, by a process comprising reacting a protein-binding ligand material containing chlorotriazinyl or related groups with an aqueous suspension of a non-cellulosic matrix containing free hydroxy or amino groups in the presence of an alkali metal hydroxide at at least pH 8, and subsequently washing the resulting solid medium to remove unreacted dye.

Protein-binding ligands described in U.K. Pat. No. 2015552 include material containing a mono or dichloro triazinyl group or related group, in particular, the so-called triazinyl dyes such as those sold under the trade marks "Cibacron" and "Procion". These are normally triazinyl derivatives of sulphonated anthraquinones, phthalocyanines or polyaromatic azo compounds, having the structure:

wherein $R^1$ is a sulphonated group derived from anthraquinone, a substituted anthraquinone, an aromatic azo group or a phthalocyanine compound and $R^2$ is either (a) an organic group, normally a sulphonated aromatic group, especially a sulphonated phenyl group, or (b) a chlorine atom.

Although we have found that an adsorbent consisting of a triazinyl dye selected from Procion Yellow H-A, Procion Turquoise MX-G, Procion Red MX-5B, and Procion Blue MX-R, bound to an agarose matrix such as agarose beads, gives satisfactory yields of glucose 6-phosphate dehydrogenase from the enzymes extract (hereinafter for convenience referred to simply as Z. mobilis extract), we have found that an adsorbent consisting of the triazinyl dye, Procion Scarlet MX-G, bound to a matrix of Sepharose CL-4B, gives the best yields of glucose 6-phosphate dehydrogenase from Z. mobilis extract, and also adsorbs the enzyme glucokinase. We have also found that the triazinyl dye Yellow MX-3R, and preferably Yellow MX-4R, bind pyruvate kinase selectively, and that the triazinyl dye Yellow MX-GR is particularly suitable for binding fructokinase.

Preferably, the Z. mobilis extract is applied to a column of the selected dye for the selected enzyme, coupled to the matrix support, or, applied to a succession of columns of selected dyes for the selected enzymes, coupled to the matrix supports, in a buffer at a pH between pH 5.6–6.0 and containing about 5 to 20 mg/ml protein. Preferably, the extraction buffer applied to the column(s) contains 1 to 10 mM $MgCl_2$.

PRACTICAL EMBODIMENTS OF THE INVENTION

Details of the process of extraction of Z. mobilis cells paste to provide the raw material for isolation and purification of the enzymes, in particular glucose 6-phosphate dehydrogenase, in accordance with that aspect of the present invention, are set out below, the optimum conditions for such extraction being apparent from a comparison of Examples 1 to 32 of Table I below, in which Examples 1–20 represent a set of results obtained in the extraction of "tough" Z. mobilis cells under the conditions so indicated, while Examples 21–32 represent a set of results obtained in the extraction of "weak" Z. mobilis cells under the conditions so indicated.

The extraction procedure in each of Examples 1 to 32 was as follows: 10 g wet weight of Z. mobilis cells were suspended in 40 ml of extraction buffer consisting of 30 mM K-phosphate, pH 7.0. This was divided into three parts, the first part remaining at pH 7, the second part adjusted to pH 7.8, and the third part adjusted to pH 8.5. Addition of the various components were as indicated in Table I below, the amount of organic solvent being 1% v/v; the amount of surfactant being 0.1% v/v; and the amount of lysozyme being 0.4 mg/g. of the cells, in each particular instance. The mixtures were incubated at 30° C. for 3 h, then centrifuged at 10,000 g for 20 min, or 4,000 g for 60 min, to remove cell debris, and the protein and enzyme activity in the supernatants measured.

TABLE I

| Example | pH | Additions | Protein (mg/ml) | Enzyme Activity (Glucose 6-phosphate dehydrogenase, units/ml) |
|---|---|---|---|---|
| 1 | 7.0 | Nil | 1.7 | 6.0 |
| 2 | 7.0 | Butanol | 2.7 | 5.5 |
| 3 | 7.0 | Nonidet | 4.9 | 10 |
| 4 | 7.0 | Butanol + Nonidet | 4.0 | 10 |
| 5 | 7.0 | Lysozyme | 1.0 | 6 |
| 6 | 7.0 | Butanol + Nonidet + Lysozyme | 12.0 | 80 |
| 7 | 7.8 | Nil | 1.5 | 6.5 |
| 8 | 7.8 | Butanol | 1.5 | 8.5 |
| 9 | 7.8 | Nonidet | 2.7 | 9 |
| 10 | 7.8 | Butanol + Nonidet | 3.1 | 9 |
| 11 | 7.8 | Lysozyme | 1.7 | 10 |
| 12 | 7.8 | Butanol + Nonidet + Lysozyme | 13.0 | 95 |

TABLE I-continued

| Example | pH | Additions | Protein (mg/ml) | Enzyme Activity (Glucose 6-phosphate dehydrogenase, units/ml) |
|---|---|---|---|---|
| 13 | 8.5 | Nil | 1.5 | 5.5 |
| 14 | 8.5 | Butanol | 2.1 | 14 |
| 15 | 8.5 | Nonidet | 2.2 | 8.5 |
| 16 | 8.5 | Butanol + Nonidet | 3.4 | 11 |
| 17 | 8.5 | Lysozyme | 3.0 | 14 |
| 18 | 8.5 | Butanol + Nonidet + Lysozyme | 15.0 | 84 |
| 19 | 8.5 | Toluene | 1.5 | 10 |
| 20 | 8.5 | Ethyl acetate | 1.5 | 7 |
| 21 | 7.0 | Nil | 0.7 | 0.0 |
| 22 | 7.0 | Nonidet + Lysozyme | 7.5 | 43 |
| 23 | 7.0 | Butanol + Lysozyme | 1.0 | 2 |
| 24 | 7.0 | Butanol + Nonidet + Lysozyme | 15.0 | 71 |
| 25 | 7.8 | Nil | 1.8 | 4.0 |
| 26 | 7.8 | Nonidet + Lysozyme | 13.0 | 68 |
| 27 | 7.8 | Butanol + Lysozyme | 1.8 | 5 |
| 28 | 7.8 | Butanol + Nonidet + Lysozyme | 15.0 | 70 |
| 29 | 8.5 | Nil | 1.0 | 2.0 |
| 30 | 8.5 | Nonidet + Lysozyme | 15.5 | 93 |
| 31 | 8.5 | Butanol + Lysozyme | 4.0 | 14 |
| 32 | 8.5 | Butanol + Nonidet + Lysozyme | 16.0 | 105 |

From these examples it is clear that only the combination of water-miscible solvent (butanol)+nonionic surfactant (Nonidet)+lysozyme achieved satisfactory extraction of "tough" Z. mobilis cells, whilst comparable results were obtained with the more easily extractable "weak" Z. mobilis cells, thus providing a reliable process for extracting both "weak" and "tough" cells equally well.

Thus, Examples 6, 12, 18, 24, 28 and 32, in which the extraction medium comprises n-butanol (1% v/v), nonionic surfactant (0.1% v/v), and lysozyme (0.4 mg/g of cells), at a pH ranging between 7.0–8.5, will be seen to be the optimum condition for glucose 6-phosphate dehydrogenase. The other enzymes mentioned above are also extracted by these conditions.

Details of the process of isolation and purification of the glucose 6-phosphate dehydrogenase and glucokinase in the extract of the Z. mobilis cells paste, in accordance with that aspect of the present invention, are set out below, the dye and the support matrix of the adsorbent system found to give optimum isolation and purification being apparent from Table II.

Procion dyes used in developing the isolation and purification process of the present invention are commercial dyes. The dyes were coupled to Sepharose Cl-4B according to the procedure of Atkinson et al [(1981) Biochem. Soc. Trans 9, 290–293]. The trade names and Colour Index Constitution Numbers (CICN) or Reactive Numbers of certain of these dyes are as follows:

| | |
|---|---|
| Procion Scarlet MX-G: CICN No. 17908; | Procion Yellow H-A: CICN No. 13245; |
| Procion Turquoise MX-G: Reactive Blue No. 140; | Procion Red MX-5B: CICN No. 18200; |
| Procion Blue MX-R: CICN No. 61205; | Procion Red MX-2B: CICN No. 18158; |
| Procion Yellow MX-6G: CICN No. 18971; | Procion Yellow MX-4R: Reactive Orange No. 14; |
| Procion Yellow MX-3R: Reactive Orange No. 86; | Procion Yellow MX-GR: Reactive Yellow No. 7. |

In developing the isolation and purification process of the present invention, an investigation of approximately fifty (50) dyes coupled to Sepharose CL-4B was carried out and revealed that: the absence of phosphate from the buffer solution containing the microorganisms extract to be applied to the dye column and the buffer used in equilibrating the dye column, resulted in an increase in the amount of protein being bound to the dye column; the amount of protein binding to the dye column increased as the pH of the buffer was lowered from 6.5 to 6.0; glucose 6-phosphate dehydrogenase bound strongly to most of the dye columns and in many instances M salt was required to elute the glucose 6-phosphate dehydrogenase from the dye column. Pyruvate kinase and fructokinase bound to less than half of the columns investigated.

Glucose 6-phosphate dehydrogenase and glucokinase bind well even to dyes which do not have a high affinity for proteins in general. These dyes include: Blue HE-G; Blue MX-R; Blue MX-7RX; Blue 2-RA; Red MX-2B; Red MX-5B; Rubine H-BN; Scarlet MX-G; Turquoise H-A; Turquoise MX-G; Yellow H-A; Yellow MX-6B and Yellow MX-8G. Although it had previously been found that glucose 6-phosphate dehydrogenase could be eluted successfully from Yellow H-A dye columns using NADP, the capacity of Yellow H-A dye columns for binding proteins is not high, and the application of more than about 15 mg of protein per cm$^3$ of column resulted in the column being overloaded, and no more binding of glucose 6-phosphate dehydrogenase could be achieved.

We thus found that it is necessary to balance the general lower affinity to bind proteins with the requirement that the dye column bind all of the glucose 6-phosphate dehydrogenase loaded onto the column. Under high protein loading conditions of 42 mg of extract protein applied to 2 cm$^3$ columns, the testing of seven dyes in Table II below shows that only two of the dyes, Blue HE-G and Scarlet MX-G, retained more than 90% of the glucose 6-phosphate dehydrogenase under those conditions, and that of these two dyes, Scarlet MX-G gave optimum recovery by elution. It was subsequently determined that glucokinase was not totally retained by these dyes at pH 6.5.

TABLE II

| Example | Dye | Units of glucose 6-phosphate dehydrogenase applied to each column = 140 | | | | |
|---|---|---|---|---|---|---|
| | | Units in: (a) | (b) | (c) | (d) | Total Recovered |
| 33 | Blue HE-G | 10 | 0 | 12 | 60 | 82 |
| 34 | Red MX-5B | 87 | 60 | 0 | 0 | 147 |
| 35 | Scarlet MX-G | 10 | 35 | 45 | 45 | 135 |
| 36 | Turquoise H-A | 100 | 32 | 10 | 2 | 144 |
| 37 | Turquoise MX-G | 27 | 38 | 48 | 17 | 130 |
| 38 | Yellow H-A | 32 | 70 | 32 | 2 | 154 |
| 39 | Yellow MX-6G | 65 | 12 | 8 | 0 | 85 |

(a) Not adsorbed in 20 mM K-phosphate pH 6.5
(b) Eluted with 1 mM NAD$^+$ in 20 mM K-phosphate pH 6.5
(c) Washed with 0.2 M K-phosphate pH 6.5
(d) Eluted with 1 mM NAD$^+$ in 0.2 M K-phosphate pH 6.5.

Further investigation of the isolation and purification of the enzyme glucose 6-phosphate dehydrogenase was accordingly confined to using the dye Scarlet MX-G, in which 2 cm$^3$ columns of Scarlet MX-G adsorbent were equilibrated in different buffers as shown in Table III. 80 mg of extract containing 240 units of glucose 6-phosphate dehydrogenase was applied to each of these columns, which is a considerably higher loading compared with the previous examples. The columns were then each washed with 50 mM K-phosphate pH 6.5, followed by elution with nucleotide substrate (1 mM NAD$^+$ or 0.1 mM NADP$^+$).

TABLE III

| Example | Buffer | Units not adsorbed | Units eluted with pH 6.5 buffer | Units eluted with nucleotide | Total Units recovered |
|---|---|---|---|---|---|
| 40 | 20 mM K-phosphate pH 6.5 | 40 | 77 | 120 (NAD) | 240 |
| 41 | 20 mM K-phosphate pH 6.5+ 2 mM MgCl$_2$ | 15 | 80 | 160 (NAD) | 255 |
| 42 | 20 mM K-phosphate pH 6.0+ 2 mM MgCl$_2$ | 0 | 50 | 210 (NADP) | 260 |

These investigations revealed that: (i) the presence of magnesium chloride in the equilibration buffer increased the adsorption of the enzyme to the dye column; (ii) 0.1 mM NADP$^+$ was at least as effective as 1 mM NAD$^+$ in eluting glucose 6-phosphate dehydrogenase from the dye column; (iii) at pH 6.0 all the glucose 6-phosphate dehydrogenase was retained. In addition, all of the glucokinase was retained on the column at this pH.

A larger scale integrated extraction/isolation/purification process for the production of glucose 6-phosphate dehydrogenase, glucokinase, pyruvate kinase and fructokinase in accordance with the present invention, was then evolved as described below, read in conjunction with the accompanying drawings, in which FIG. 1 graphically illustrates the elution of glucokinase and glucose 6-phosphate dehydrogenase from Scarlet MX-G column, buffers being changed as indicated by the arrows.

Extraction 700 g Z. mobilis (strain ZM4) cells were suspended in an aqueous medium containing 30 mM K-phosphate, pH 7.0, 1% v/v n-butanol, 0.1% v/v Nonidet P40 and 0.4 mg/g of lysozyme based on the cells, giving 2800 ml of 83 units/ml glucose 6-phosphate dehydrogenase.

Primary Isolation Stage

The extract obtained as above, adjusted to pH 6.0, was applied to a column of Scarlet MX-G/Sepharose CL-4B of dimensions ca. 32 cm$^2$ × 24 cm (750 cm$^3$), and washed-in with 2000 ml of pH 6.0 buffer (10 mM KOH-morpholino ethane sulphonate pH 6.0 containing 30 mM NaCl and 2 mM MgCl$_2$).

The buffer wash was changed to 30 mM K-phosphate containing 2 mM MgCl$_2$, pH 7.0, and washing continued until little or no protein was emerging from the column as determined by absorbance at 280 nm. The protein eluted by the change of buffer was analysed for glucokinase activity, and this was to emerge in the latter part of the protein peak (FIG. 1).

Figure 1:
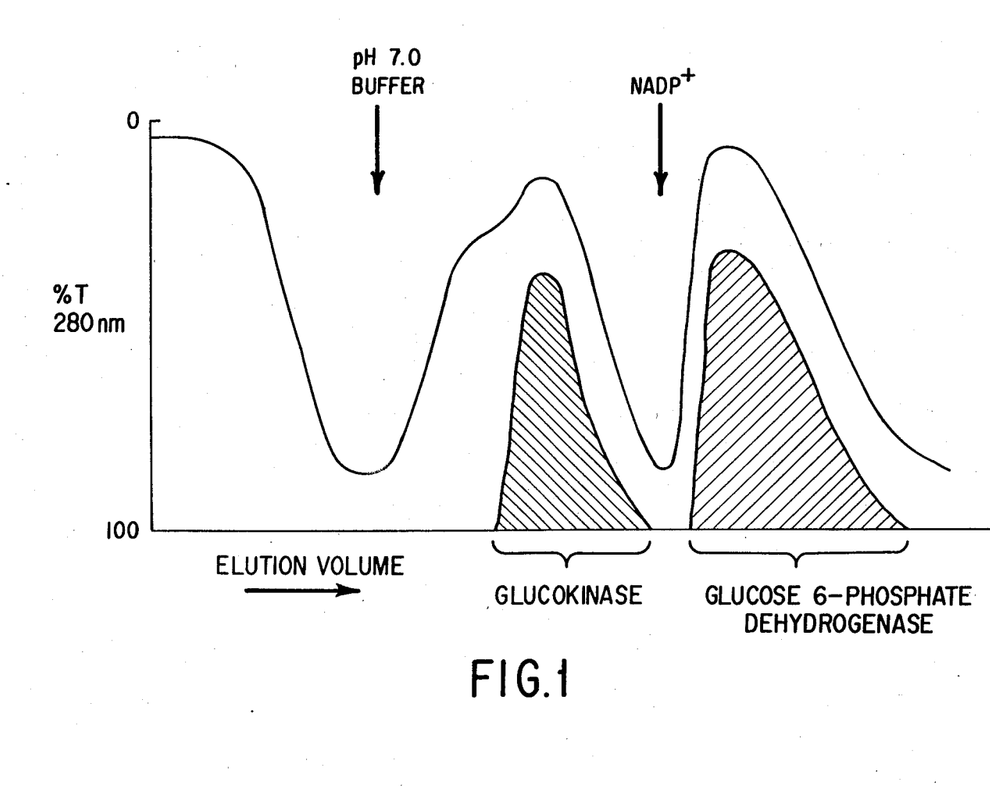

Fractions with glucokinase activity were collected and concentrated for additional purification as set out below. 750 ml of K-phosphate buffer pH 7.0 containing 0.2 mM NADP$^{30}$ was then applied to the column, and the peak containing the glucose 6-phosphate dehydrogenase was collected (FIG. 1).

Figure 2:
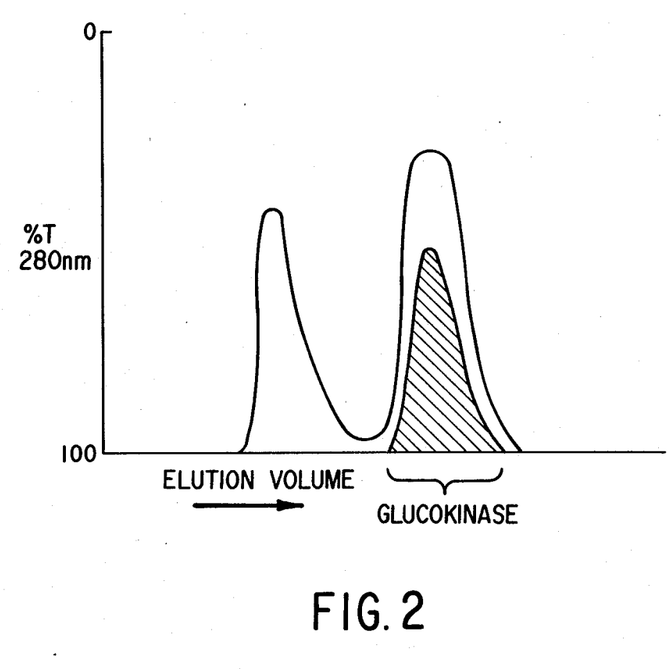
FIG. 2 graphically illustrates the purification of the glucokinase fraction on Sephacryl S-200 column.

Glucokinase was concentrated by ultrafiltration to between 10 and 15 mg protein/ml. It was further purified by one of two alternative procedures: (i) the sample was applied to a column of Sephacryl S-200 (25 cm$^2 \times$80 cm) and separation from impurities was achieved by gel filtration, the glucokinase activity being associated with the second peak (FIG. 2); or (ii) to every 100 ml of the concentrated solution, 22 g powdered ammonium sulphate was dissolved in. After 20–30 min, the precipitated protein (glucokinase) was collected by centrifuging at 15,000 g for 30 min. The gelatinous precipitate was transferred to a suitable container for long-term storage at 4° C. using a minimal amount of water to rinse the centrifuge tubes.

Figure 3:
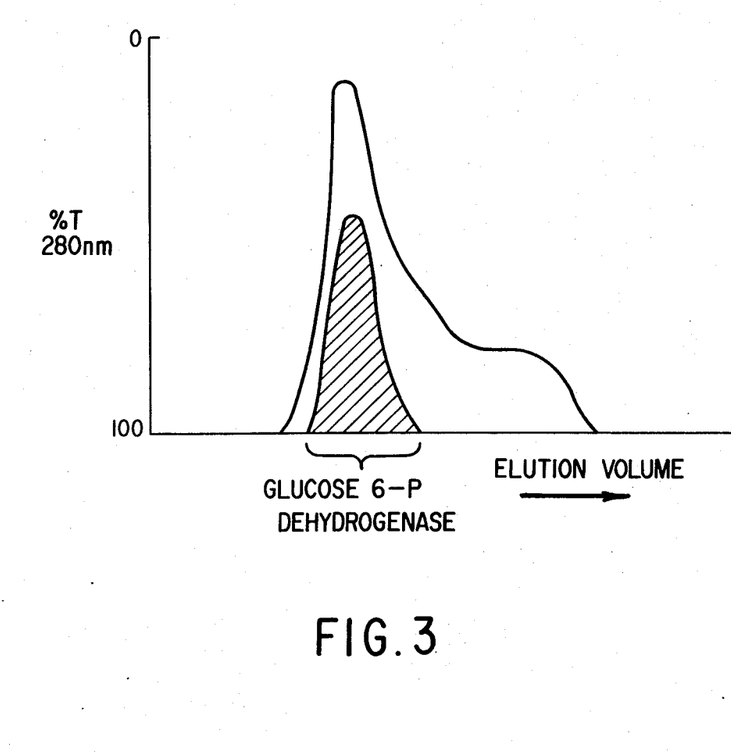
FIG. 3 graphically illustrates the purification of the glucose 6-phosphate dehydrogenase fraction on Sephacryl S-200 column.

Glucose 6-phosphate dehydrogenase was similarly further purified by one of two alternative procedures after concentration by ultrafiltration: (i) the sample was applied to the Sephacryl S-200 column described above, the glucose 6-phosphate dehydrogenase separating from the contaminants (FIG. 3); or, (ii) to every 100 ml, 30 g powdered ammonium sulphate was dissolved in, and the enzyme was collected and stored as described above.

A summary of the isolation of glucose 6-phosphate dehydrogenase and glucokinase is contained in Table IV below:

TABLE IV

Primary Isolation Stage
Isolation of glucose 6-phosphate dehydrogenase and glucokinase from the extract

| Fraction | Volume ml | Protein mg | Glucokinase Total k units | Glucokinase Specific activity units/mg | Glucose 6-phosphate dehydrogenase Total k units | Glucose 6-phosphate dehydrogenase Specific activity units/mg |
|---|---|---|---|---|---|---|
| Crude Extract | 2800 | 36000 | 98 | 2.7 | 232 | 6.4 |
| Not adsorbed on Scarlet MX-G | 3500 | 25000 | 0 | — | 0 | — |
| Eluted with pH 7.0 phosphate buffer | 400 | 670 | 80 | 120 | 0 | — |
| Eluted with NADP | 550 | 610 | 0 | — | 209 | 345 |
| After S-200 gel filtration (glucokinase) | 150 | 290 | 65 | 220 | 0 | — |
| After S-200 gel filtration (glucose 6-P dehydrogenase) | 150 | 365 | 0 | — | 190 | 520 |

Glucose 6-phosphate dehydrogenase isolated from Z. mobilis is physiologically an NAD-linked dehydrogenase though it also shows activity with NADP. The properties of that enzyme are very similar to the properties of glucose 6-phosphate dehydrogenase isolated from L. mesenteroides [Olive, C. and Levy H. R. (1967) Biochemistry, 6, 730–736].

The best specific activity of glucose 6-phosphate dehydrogenase isolated by the present procedure from Z. mobilis so far obtained is 500±20 units/mg at 25° C. in the assay conditions of: 50 mM Tris-Cl buffer, pH 8.0; 1 mM glucose 6-phosphate; 1 mM NAD$^+$. With 1 mM NADP$^+$, the activity of this enzyme is approximately 70% of the value with NAD$^+$. However, the Km for NADP$^+$ at 0.04 mM is 5-fold lower than that for NAD$^+$, 0.21 mM, and the Km for glucose 6-phosphate dehydrogenase is 0.17 mM.

Glucose 6-phosphate dehydrogenase so obtained has a high extinction coefficient at 280 nm (1.75 for 1 mg/ml solution). Treatment with DTNB fails to react any sulphydryls. However, on denaturation with sodium dodecyl sulphate, two sulphydryls per subunit are exposed and react rapidly. A sub-unit molecular weight of 52,000 and its elution position on S-200 suggests that the native enzyme may be tetrameric in 30 mM phosphate buffer pH 7. The enzyme has low solubility in ammonium sulphate and crystallizes from a gelatinous suspension at about 30% saturation of ammonium sulphate, and appears to be very stable in this state.

Glucokinase so obtained is almost homogenous by electrophoretic criteria. The enzyme is a dimer, molecular weight 2×32,000. Its specific activity is 220±10 units/mg at 25° C. in the assay conditions of: 50 mM K-Morpholinopropane sulphonate, 30 mM NaCl, 2 mM MgCl$_2$, pH 6.8; 5 mM glucose, 1 mM ATP, 1 mM NAD$^+$ and 2 units ml$^{-1}$ glucose 6-P dehydrogenase. The Km values are (approximately) glucose: 0.2 mM; ATP 0.8 mM. The enzyme is inactive with, and in not inhibited by, 10 mM concentrations of the following: fructose, sucrose, galactose, mannose, 2-deoxyglucose, xylose, ribose, sorbitol, glycerol, or gluconate. Although preliminary investigations indicate that the enzyme has an unusually large number of sulphydryl groups, it is not highly suscepible to oxidative inactivation, nor have patially inactivated preparations been reactivated by thiol compounds.

Secondary and Tertiary Isolation Stages

Subsequent to passage through te Scarlet MX-G column for isolating glucose 6-phosphate dehydrogenase and glucokinase, all the pyruvate kinase and fructokinase in the original extract are still present. Two further columns are used to successively remove these enzymes. We have thus found that the dyes Yellow MX-4R and Yellow MX-3R are highly specific for pyruvate kinase. Fructokinase passes through columns containing these dyes, but can be retained on several other dyes that bind proteins more strongly. The most satisfactory of these is Yellow MX-GR, which adsorbs all the fructokinase, yet allows a material proportion of the remaining proteins through.

Affinity chromatography adsorbent columns of the same cross-sectional area as used for the isolation of glucose 6-phosphate dehydrogenase and glucokinase, appropriate for the isolation of pyruvate kinase and fructokinase, respectively, are placed in series. After the extract has been applied and washed in with sufficient starting (pH 6.0) buffer, the columns are disconnected and separately worked-up.

Pyruvate kinase adsorbed to the Yellow MX-4R column is eluted by the following procedure: The column is washed with 3 column volumes of pH 7.0 buffer (30 mM K-phosphate+2 mM MgCl$_2$, pH 7.0), followed by 1 column volume of the same buffer containing 0.2 mM phosphoenol pyruvate, followed by a further column volume of buffer without phosphoenol pyruvate. Pyruvate kinase is specifically eluted by its substrate; the active fractions may be concentrated by ultrafiltration, and stored as required either frozen, freeze-dried, or as an ammonium sulphate suspension. The preparation as obtained from the column needs additional purification, as it is homogenous electrophoretically. Specific activity measured in 50 mM K-morpholinopropane sulphonate, 0.15M KCl, 2 mM MgCl$_2$ pH 6.8, containing 1 mM ADP, 1 mM phosphoenolpyruvate, 0.15 mM NADH and 2 units ml$^{-1}$ lactate dehydrogenase is 300 units mg$^{-1}$ at 25° C. No allosteric effectors are required for enzyme activity. It is stable for long periods as a crystalline ammonium sulphate suspension.

Figure 4:
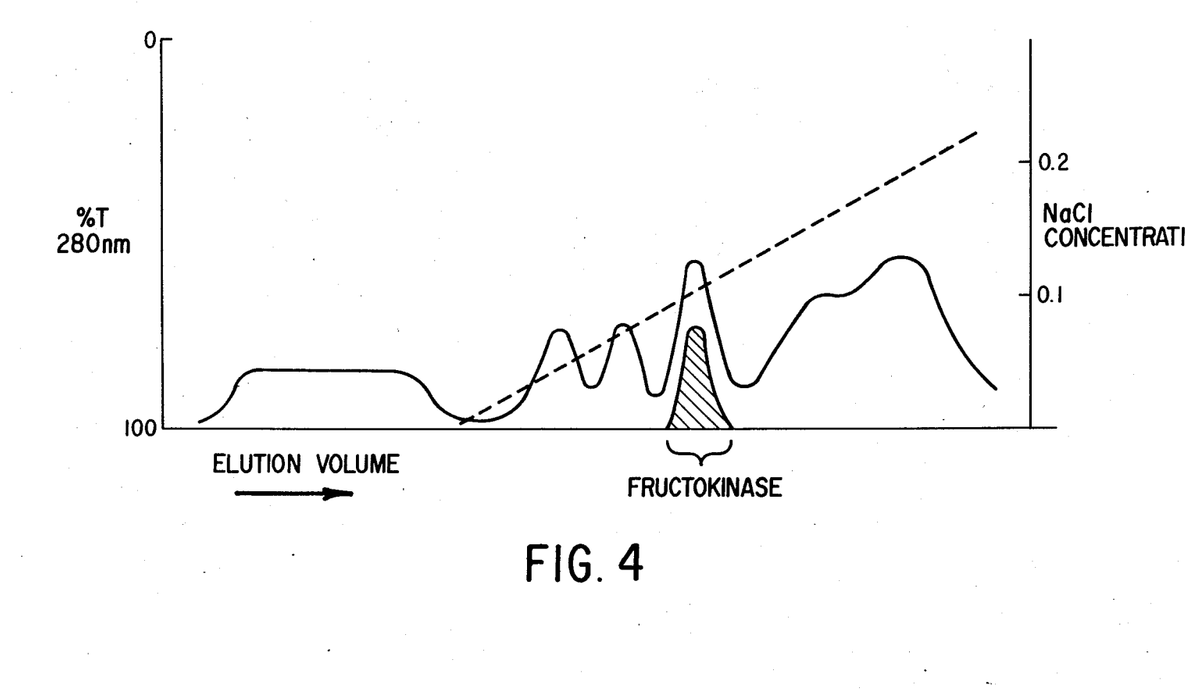
FIG. 4 graphically illustrates the purification of the fructokinase fraction on DEAE-cellulose column, using a gradient of NaCl.

Fructokinase bound to the third column, Yellow MX-GR, is eluted by the following procedure. The column is washed with 2 column volumes 30 mM K-morpholinoethane sulphonate, 30 mM NaCl, 2 mM MgCl$_2$, pH 6.5. The enzyme is then eluted with 1.5 column volume of the same buffer containing 2 mM ATP. The active fractions are collected, but the enzyme is not very pure at this stage. The pH of the eluted enzyme is adjusted to 8.0 with 1M tris, and it is run on to a DEAE-cellulose column pre-equilibrated in 20 mM tris-chloride, pH 8.0. The enzyme adsorbs, and can be eluted by a salt gradient created with 0.25M NaCl in tris buffer, approximately 4× the column volume. Fructokinase elutes at about 0.1M Nacl, and most impurities are separated (FIG. 4).

The active enzyme may be concentrated by ultrafiltration and stored frozen or freeze-dried. Best specific activities have been in the range 250–300 units mg$^{-1}$, in the assay conditions of 50 mM K-morpholino propane sulphonate buffer, 30 mM NaCl, 2 mM MgCl$_2$ pH 6.8 containing 1 mM ATP, 5 mM fructose, 1 mM NAD$^+$, 2 unit ml$^{-1}$ glucose 6-phosphate dehydrogenase and 2 unit ml$^{-1}$ phosphoglucose isomerase. The enzyme is a dimer, molecular weight 2×28,000, and is quite stable on storage. Km values are: fructose 0.5 mM, ATP 0.4 mM. The enzyme is inactive with, and is not inhibited by, 10 mM concentration of the following: mannose, sucrose, galactose, xylose, ribose, 2-deoxyglucose, gluconate, sorbitol or glycerol. However, glucose is a strong competitive inhibitor with fructose, Ki 0.2 mM. Thus, with low levels of fructose, the enzyme is essentially inactive in the presence of glucose at a concentration of 5–10 mM or more.

A summary of the isolation of pyruvate kinase and fructokinase is contained in Table V below:

TABLE V

Secondary and Tertiary Extraction Stages
Isolation of pyruvate kinase and fructokinase from extracted fraction

| Fraction | Volume ml | Protein mg | Pyruvate kinase Total K units | Pyruvate kinase Specific Activity units/mg | Fructokinase Total K units | Fructokinase Specific Activity units/mg |
|---|---|---|---|---|---|---|
| Not adsorbed on Scarlet MX-G | 500 | 3600 | 130 | 36 | 7.5 | 2.1 |
| Not adsorbed on Yellow MX-4R | 600 | 2800 | 5 | — | 7.0 | 2.5 |
| Not adsorbed on Yellow MX-GR | 700 | 1900 | 0 | — | 0.5 | — |
| Eluted from Yellow MX-4R by phosphoenol pyruvate | 120 | 320 | 95 | 300 | 0 | — |
| Eluted from Yellow MX-GR by ATP | 170 | 135 | 0 | — | 6.0 | 45 |
| Peak from DEAE-cellulose | 30 | 22 | 0 | — | 5.5 | 250 |

I claim:

1. A process for the preparation of an enzyme extract containing glucose 6-phosphate dehydrogenase and derived from microorganism cells, which comprises subjecting *Zymomonas mobilis* bacterium cells to extraction with an extraction medium comprising a partially water-miscible organic solvent; a non-ionic surfactant; and lysozyme; under neutral to alkaline pH conditions to provide an extract containing said enzyme.

2. A process according to claim 1 wherein the enzyme extract also contains glucokinase, pyruvate kinase and fructokinase.

3. A process according to claim 1 or 2 wherein the partially water-miscible organic solvent is present in an amount of about 1–2% v/v; the non-ionic surfactant is present in an amount of about 0.05–0.2% v/v; the lysozyme is present in an amount of about 0.2 to 2 mg/g wet wt. of the *Zymomonas mobilis* cells; and the pH of the extraction medium is between 7.0 and 9.0.

4. A process according to claim 1 or 2 wherein the partially water-miscible organic solvent is present in an amount of about 1% v/v; the non-ionic surfactant is present in an amount of about 0.1% v/v; the lysozyme is present in an amount of about 0.2 to 2 mg/g wet wt. of the *Zymomonas mobilis* cells; and the pH of the extraction medium is between 7.5 and 8.5.

5. A process according to claim 1 or 2 wherein the partially water-miscible organic solvent is selected from aromatic hydrocarbons, lower alkyl esters and lower alkanols; and the non-ionic surfactant is a phenyl polyethylene glycol.

6. A process according to claim 1 or 2 wherein the partially water-miscible organic solvent is selected from toluene, ethyl acetate and butan-1-ol; and the non-ionic surfactant is a phenyl polyethylene glycol selected from those identified by the trade names Triton and Nonidet.

7. A process according to claim 1 or 2 wherein the glucose 6-phosphate dehydrogenase is isolated from the enzyme extract by contacting said extract in a buffer with an affinity chromatography adsorbent which is a protein-binding dye bound to a support matrix and selective with respect to glucose 6-phosphate dehydrogenase so that glucose 6-phosphate dehydrogenase is selectively isolated from said extract by said affinity chromatography adsorbent, followed by elution to recover the glucose 6-phosphate dehydrogenase from said affinity chromatography adsorbent, with optional purification of the eluted glucose 6-phosphate dehydrogenase.

8. A process according to claim 7 wherein the affinity chromatography adsorbent consists of a selective triazinyl protein-binding dye bound to a support matrix chosen from polymers and copolymers of agarose, dextrans and amides, glass beads and nylon matrices.

9. A process according to claim 7 wherein the affinity chromatography adsorbent is a triazinyl protein-binding dye chosen from those having the identification Colour Index Constitution No. 17908 conforming with the trade name Procion Scarlet MX-G; the identification Colour Index Constitution No. 13245 conforming with the trade name Procion Yellow H-A; the identification Reactive Blue No. 140 conforming with the trade name Procion Turquoise MX-G; the identification Colour Index Constitution No. 18200 conforming with the trade name Procion Red MX-5B; the identification Colour Index Constitution No. 61205 conforming with the trade name Procion Blue MX-R; the identification Colour Index Constitution No. 18158 conforming with the trade name Procion Red MX-2B; and the identification Colour Index Constitution No. 18971 conforming with the trade name Procion Yellow MX-6G; in each case bound to a support matrix.

10. A process according to claim 7 wherein said extract is in a phosphate buffer at between pH 5.6–6.0 and containing between 5–20 mg ml$^{-1}$ protein and is passed through a column of said affinity chromatography adsorbent; excess protein is then washed out with a further amount of said buffer; and the column is then washed with phosphate buffer at about pH 7.0 before elution of the glucose 6-phosphate dehydrogenase.

11. A process according to claim 7 wherein said extract in a phosphate buffer contains 1–10 mM $MgCl_2$.

12. A process according to claim 10 wherein the glucose 6-phosphate dehydrogenase is eluted from said affinity chromatography adsorbent by nicotinamide adenine dinucleotide phosphate at a concentration between 0.05–0.5 mM, in phosphate buffer at about pH 7.0.

13. A process according to claim 12 wherein the eluted glucose 6-phosphate dehydrogenase is purified suitably by gel filtration on a column of Sephacryl S-200.

14. A process for the sequential isolation of the enzymes glucose 6-phosphate dehydrogenase, glucokinase, pyruvate kinase and fructokinase, present in an enzyme extract obtained from *Zymomonas mobilis* bacterium cells, which comprises sequentially contacting the extract in a buffer with a plurality of affinity chromatography adsorbents each of which is a protein-binding dye bound to a support matrix and selective with respect to said enzymes so that glucose 6-phosphate dehydrogenase and glucokinase are isolated from the extract by the correspondingly selective adsorbent, followed by isolation of pyruvate kinase and fructokinase by the correspondingly selective adsorbents, then elution to recover each enzyme from the correspondingly selective adsorbent of said plurality of adsorbents, with optional purification of each enzyme.

15. A process according to claim 14 wherein the buffered extract sequentially contacts a primary isolation stage affinity chromatography adsorbent for selective isolation of glucose 6-phosphate dehydrogenase and glucokinase, a secondary isolation stage affinity chromatography adsorbent for selective isolation of pyruvate kinase, and a tertiary isolation stage affinity chromatography adsorbent for selective isolation of fructokinase, each said adsorbent consisting of a selective triazinyl protein-binding dye bound to a support matrix chosen from polymers and copolymer of agarose, dextrans and amides, glass beads, and nylon matrices.

16. A process according to claim 15 wherein the buffered extract contacts the triazinyl protein-binding dye having the identification Colour Index Constitution No. 17908 conforming with the trade name Procion Scarlet MX-G bound to a support matrix, as affinity chromatography adsorbent for selective isolation of glucose 6-phosphate dehydrogenase and glucokinase in the primary isolation stage.

17. A process according to claim 16 wherein the primary isolation stage affinity chromatography adsorbent is washed with a buffer containing about 30 mM K-phosphate and about 2 mM $MgCl_2$ at pH 7.0 to elute the glucokinase fraction.

18. A process according to claim 16 wherein the primary isolation stage affinity chromatography adsorbent is washed with a K-phosphate buffer at pH 7.0 containing about 0.2 mM $NADP^{30}$ to elute the glucose 6-phosphate dehydrogenase fraction.

19. A process according to claim 16 wherein the buffered extract from the primary isolation stage contacts the triazinyl protein-binding dye having the identification Reactive Orange No. 14 conforming with the trade name Procion Yellow MX-4R, or the triazinyl protein-binding dye having the identification Reactive Orange No. 86 conforming with the trade name Procion Yellow MX-3R, bound in each case to a support matrix, as affinity chromatography adsorbent for selective isolation of pyruvate kinase in the secondary isolation stage.

20. A process according to claim 19 wherein the secondary isolation stage affinity chromatography adsorbent is washed with a buffer containing about 30 mM K-phosphate and about 2 mM $MgCl_2$ at pH 7.0 to elute the pyruvate kinase fraction.

21. A process according to claim 16 wherein the buffered extract from the secondary isolation stage contacts the triazinyl protein-binding dye having the identification Reactive Yellow No. 7 conforming with the trade name Procion Yellow MX-GR, bound to a support matrix, as affinity chromatography adsorbent for selective isolation of fructokinase in the tertiary isolation stage.

22. A process according to claim 19 wherein the tertiary isolation stage affinity chromatography adsorbent is washed with a buffer containing about 30 mM K-morpholinoethane sulphonate, about 30 mM NaCl, and about 2 mM $MgCl_2$ at pH 6.5 to elute the fructokinase fraction.

23. An integrated process for the preparation of the enzymes glucose 6-phosphate dehydrogenase, glucokinase, pyruvate kinase and fructokinase, by extraction of microorganism cells to provide an enzyme extract containing said enzymes, followed by the sequential isolation of those enzymes from said extract, which comprises: (A) subjecting *Zymomonas mobilis* bacterium cells to extraction with an extraction medium comprising a partially water-miscible organic solvent; a nonionic surfactant; and lysozyme; under neutral to alkaline pH conditions to provide an extract containing said enzymes; (B) sequentially contacting the extract in a buffer with a plurality of affinity chromatography adsorbents each of which is a a protein-binding dye bound to a support matrix and individually selective with respect to each of said enzymes so that glucose 6-phosphate dehydrogenase and glucokinase are isolated from the extract by the correspondingly selective adsorbent, followed by isolation of pyruvate kinase and fructokinase by the correspondingly selective adsorbents; then (C) elution to recover each enzyme from the correspondingly selective adsorbent of said plurality of adsorbents, with optional purification of each enzyme.

24. A process according to claim 23 wherein the partially water-miscible organic solvent is present in an amount of about 1–2% v/v; the non-ionic surfactant is present in an amount of about 0.05–0.2% v/v; the lysozyme is present in an amount of about 0.2 to 2 mg/g wet wt. of the *Zymomonas mobilis* cells; and the pH of the extraction medium is between 7.0 and 9.0.

25. A process according to claim 23 wherein the partially water-miscible organic solvent is present in an amount of about 1% v/v; the non-ionic surfactant is present in an amount of about 0.1% v/v; the lysozyme is present in an amount of about 0.2 to 2 mg/g wet wt. of the *Zymomonas mobilis* cells; and the pH of the extraction medium is between 7.5 and 8.5.

26. A process according to claim 23 wherein the partially water-miscible organic solvent is selected from aromatic hydrocarbons, lower alkyl esters and lower alkanols; and the non-ionic surfactant is a phenyl polyethylene glycol.

27. A process according to claim 23 wherein the partially water-miscible organic solvent is selected from toluene, ethyl acetate and butan-1-ol; and the non-ionic surfactant is a phenyl polyethylene glycol selected from those identified by the trade names Triton and Nonidet.

28. A process according to claim 23 wherein the buffered extract sequentially contacts a primary isolation stage affinity chromatography adsorbent for selective isolation of glucose 6-phosphate dehydrogenase and glucokinase, a secondary isolation stage affinity chromatography adsorbent for selective isolation of pyruvate kinase, and a tertiary isolation stage affinity chromatography adsorbent for selective isolation of fructokinase, each said adsorbent consisting of a selective triazinyl protein-binding dye bound to a support matrix chosen from polymers and copolymers of agarose, dextrans and amides, glass beads, and nylon matrices.

29. A process according to claim 28 wherein the buffered extract contacts the triazinyl protein-binding dye having the identification Colour Index Constitution No. 17908 conforming with the trade name Procion Scarlet MX-G bound to a support matrix, as affinity chromatography adsorbent for selective isolation of glucose 6-phosphate dehydrogenase and glucokinase in the primary isolation stage.

30. A process according to claim 28 wherein the primary isolation stage affinity chromatography adsorbent is washed with a buffer containing about 30 mM K-phosphate and about 2 mM $MgCl_2$ at pH 7.0 to elute the glucokinase fraction.

31. A process according to claim 28 wherein the primary isolation stage affinity chromatography adsorbent is washed with a K-phosphate buffer at pH 7.0 containing about 0.2 mM $NADP^+$ to elute the glucose 6-phosphate dehydrogenase fraction.

32. A process according to claim 28 wherein the buffered extract from the primary isolation stage contacts the triazinyl protein-binding dye having the identification Reactive Orange No. 14 conforming with the trade name Procion Yellow MX-4R, or the triazinyl protein-binding dye having the identification Reactive Orange No. 86 conforming with the trade name Procion Yellow MX-3R, bound in each case to a support matrix, as affinity chromatography adsorbent for selective isolation of pyruvate kinase in the secondary isolation stage.

33. A process according to to claim 28 wherein the secondary isolation stage affinity chromatography adsorbent is washed with a buffer containing about 30 mM K-phosphate and about 2 mM $MgCl_2$ at pH 7.0 to elute the pyruvate kinase fraction.

34. A process according to claim 28 wherein the buffered extract from the secondary isolation stage contacts the triazinyl protein-binding dye having the identification Reactive Yellow No. 7 conforming with the trade name Procion Yellow MX-GR, bound to a support matrix, as affinity chromatography adsorbent for selective isolation of fructokinase in the tertiary isolation stage.

35. A process according to claim 28 wherein the tertiary isolation stage affinity chromatography adsorbent is washed with a buffer containing about 30 mM K-morpholinoethane sulphonate, about 30 mM NaCl and about 2 mM $MgCl_2$ at pH 6.5 to elute the fructokinase fraction.

* * * * *